United States Patent [19]
Jansen et al.

[11] Patent Number: 6,093,840
[45] Date of Patent: Jul. 25, 2000

[54] SILYLALKYLBORANES, OLIGO OR POLYBOROCARBOSILAZANES AND SILICON CARBONITRIDE CERAMICS

[75] Inventors: Martin Jansen, Leonberg; Hardy Jüngermann, Werl, both of Germany

[73] Assignee: Bayer Aktiengesellschaft, Leverkusen, Germany

[21] Appl. No.: 09/402,038

[22] PCT Filed: Mar. 23, 1996

[86] PCT No.: PCT/EP98/01669

§ 371 Date: Sep. 27, 1999

§ 102(e) Date: Sep. 27, 1999

[87] PCT Pub. No.: WO98/45302

PCT Pub. Date: Oct. 15, 1998

[30] Foreign Application Priority Data

Apr. 3, 1997 [DE] Germany ............... 197 13 766

[51] Int. Cl.[7] .................... C07F 5/02; C07F 7/08
[52] U.S. Cl. ................ 556/402; 528/5; 423/276; 501/96; 501/97; 501/96.1; 501/96.3; 501/96.5
[58] Field of Search .............. 556/402; 423/276; 501/96, 97, 96.1, 96.3, 96.5; 528/5

[56] References Cited

U.S. PATENT DOCUMENTS

| | | | |
|---|---|---|---|
| 2,831,009 | 4/1958 | Seyferth | 556/402 |
| 3,154,520 | 10/1964 | Dupont et al. | 556/402 |
| 4,851,491 | 7/1989 | Riicitiello et al. | 556/402 X |
| 4,987,201 | 1/1991 | Riccitiello et al. | 556/402 X |
| 5,030,744 | 7/1991 | Funayama et al. | 556/402 |
| 5,233,066 | 8/1993 | Jansen et al. | 556/402 |
| 5,312,942 | 5/1994 | Jansen et al. | 556/402 |
| 5,405,982 | 4/1995 | Loffelholz et al. | 556/402 X |
| 5,866,705 | 2/1999 | Jansen et al. | 556/402 |

OTHER PUBLICATIONS

Applied Organometallic Chemistry, vol. 10, (month unavailable) 1996, pp. 241–256.

Ralf Riedel, Joachim Bill and Andreas Kienzle, Boron-modified Inorganic Polymers–Precursors for the Synthesis of Multicomponent Ceramics.

*Primary Examiner*—Paul F. Shaver
*Attorney, Agent, or Firm*—Joseph C. Gil; Diderico van Eyl

[57] ABSTRACT

Molecular silylalkylboranes, a process for their preparation, oligo- or polyborocarbosilazanes, a process for their preparation and their use and silicon carbonitride ceramics and a process for their preparation.

8 Claims, No Drawings

SILYLALKYLBORANES, OLIGO OR POLYBOROCARBOSILAZANES AND SILICON CARBONITRIDE CERAMICS

BACKGROUND OF THE INVENTION

The present invention relates to molecular silylalkylboranes, a process for their preparation, oligo- or polyborocarbosilazanes, a process for their preparation and their use and silicon carbonitride ceramics and a process for their preparation.

The process for producing multinary, non-oxidic ceramics via molecular single-component precursors has achieved outstanding importance. It has opened up the path to nitridic, carbidic and carbonitridic systems which are not accessible via conventional solid-state reactions. The products are distinguished by high purity, homogeneous distribution of elements and uniform particle size.

Materials which consist of Si, B and N and, if appropriate, also C, demonstrate particular properties with respect to thermal stability and resistance to oxidation. They can be used as bulk material or else for coatings and as fibrous material. The boron-containing materials exhibit an increased inhibition of crystallization, whereas the carbon-containing ceramics have, in addition, higher decomposition temperatures than carbon-free ceramics.

According to U.S. Pat. No. 5,233,066, synthesis of the amorphous ceramics $Si_3B_3N_7$ and $SiBN_3C$ from the precursor trichlorosilylaminodichloroborane (TADB) is achieved by crosslinking with ammonia or amines and subsequent pyrolysis in a gas stream.

In this method, the composition of the products is set firstly by the single-component precursor and secondly by the type of crosslinking. Whereas the Si:B ratio is set by the precursor to 1:1, the N:C ratio is a function of the choice of methylamine as crosslinking reagent.

The carbon is incorporated into the ceramics here via the organic amine side chain. However, this takes place in an uncontrolled manner via a reaction which has not been described in detail. The disadvantage of this procedure is the low possibility of varying the C content. Extending the side chain does not lead inevitably to a higher C content in the ceramics, but to graphite deposits in the material. This has an adverse effect on the properties. In addition, a large part of the carbon is lost during the pyrolysis, since the side chains are eliminated in the form of volatile alkanes, alkenes etc.

According to Appl. Organomet. Chem. 10 (1996) 241–256, polymeric boron-containing carbosilanes are obtained by reacting vinyl-containing polysilanes or polysilazanes with boron adducts of the formula $BH_3 \cdot SR_2$ where $R=C_1-C_{18}$-alkyl.

According to DE-A 43 20 785, trissilylalkylboranes of the formula $B[-C_2H_4-SiCl_2X]_3$ are obtained by reacting vinylsilanes of the formula $CH_2=CH-SiCl_2X$ with $BH_3 \cdot THF$.

In these methods, either polymers are obtained directly or the ratio of Si to B does not correspond to the ideal ratio of 1:1.

The object of the present invention was therefore the provision of novel precursors which are simple to prepare and provide an opportunity for the controlled introduction of carbon, without having the disadvantages of the prior art.

DESCRIPTION OF THE INVENTION

Surprisingly, the object was achieved with compounds of the type

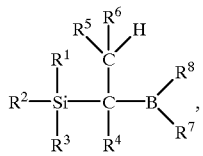

where each Si atom is coordinated to 3 radicals R and each B atom is coordinated to 2 radicals R and silicon and boron are linked by a $C(CR^5R^6H)(R^4)$ bridge, where $R^1$ to $R^3$ independently of one another are $C_1-C_6$-alkyl, vinyl, phenyl, hydrogen or halogen, $R^4$ to $R^6=C_1-C_6$-alkyl, vinyl or phenyl groups and/or hydrogen and $R^7$ and $R^8$ are chloride and/or bromide.

By means of these compounds which have already incorporated carbon in the backbone, the incorporation into the ceramics is promoted and elimination of volatile carbon compounds is reduced.

The invention therefore relates to molecular silylalkylboranes of the general structural formula

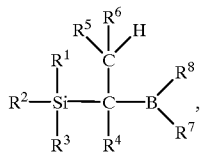

where each Si atom is coordinated to 3 radicals R and each B atom is coordinated to 2 radicals R and silicon and boron are linked by a $C(CR^5R^6H)(R^4)$ bridge, where $R^1$ to $R^3$ independently of one another are $C_1-C_6$-alkyl, vinyl, phenyl, hydrogen or halogen, $R^4$ to $R^6=C_1-C_6$-alkyl, vinyl or phenyl groups and/or hydrogen and $R^7$ and $R^8$ are chloride and/or bromide.

In a preferred embodiment of the invention, in the molecular silylalkylboranes
$R^1$ to $R^3$=Cl and/or $CH_3$,
$R^4$=H,
$R^5=CH_3$ and
$R^6$ and $R^7$=Cl.

The invention additionally relates to a process for preparing the molecular silylalkylboranes of the invention, according to which halogenovinylsilanes of the formula

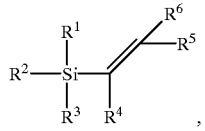

where $R^1$ to $R^3$=H, halogen, $C_1-C_6$-alkyl, vinyl or phenyl and $R^4$ to $R^6$=H, $C_1-C_6$-alkyl, vinyl or phenyl, are reacted with dihalogenoboranes where halogen=Cl and/or bromine, at temperatures between –80 and 200° C., and the reaction mixture is then subjected to fractional distillation at a pressure between 1 mbar and 20 mbar.

Dihalogenoboranes in this invention are preferably $BBr_2H$ or $BCl_2H$.

In a preferred embodiment of the process of the invention, the dihalogenoboranes are either produced in situ from silanes of the formula $R_x^1R_y^2SiH_{4-x-y}$ where $x+y<4$, $R^1=C_1-C_6$-alkyl or phenyl and $R^2$=halogen, and boron trihalides.

The halogenoboranes $HBX_2$ where $X=Cl$, Br used in the process of the invention can, in a further embodiment, alternatively be produced in situ from alkyldihalogenoboranes of the formula $RBX_2$ where $X=Cl, Br$ and $R=C_2-C_6$-alkyl by elimination of alkenes.

The in-situ preparation has the advantage that no intermediates need be isolated, but all starting materials can be reacted in the same vessel.

In addition, the in-situ generation of the dihalogenoboranes has the advantage that byproducts such as diborane are not produced or are produced only in traces.

In a preferred embodiment, the reaction is carried out at temperatures between $-80°$ C. and $200°$ C. either in the absence of solvent or in an aprotic, organic solvent, which may be a $C_5-C_8$-alkane, an acyclic or cyclic ether or an alkylaromatic.

In the case of the process without solvent, temperatures up to $50°$ C. are preferred, and in the case of the process with solvent, temperatures up to $200°$ C. are preferred.

To prepare the pure substances, the byproducts and any solvent present is removed and the product is fractionated at a pressure between 1 and 20 mbar. However, other customary purification processes can be used, such as freezing out.

The vinylsilanes used as starting products are commercially available. The dichloroborane or dibromoborane generated as an intermediate can be prepared in accordance with J. Org. Chem. 55 (1990) 2274–2275 or Organometallics 14 (1995) 4157–4166 from alkylsilanes or phenylsilanes by reaction with boron trichloride. BClBrH can also be prepared in accordance with the publications cited there.

Dichloroborane or dibromoborane can likewise be produced by reacting alkylhalogenosilanes with boron trihalides. In particular in this case, reacting chlorodimethylsilane with boron trichloride is useful.

The invention additionally relates to oligo- or polyborocarbosilazanes made from the molecular silylalkylboranes of the invention, characterized in that each silicon atom has at least one carbon atom in the first coordination sphere and that this carbon atom is bound to a boron atom, this boron atom in addition being further bound to 2 nitrogen atoms.

The invention additionally relates to a process for preparing the polymeric oligo- or polyborocarbosilazanes of the invention, in which at least one molecular silylalkylborane of the invention is reacted with at least 10 mol of ammonia and/or an organylamine of the formula $H_2NR$, where $R=H$, $C_1-C_6$-alkyl, vinyl or phenyl, per mole of silylalkylborane in a solvent at temperatures of $-80$ to $300°$ C.

The oligo- or polycarbosilazanes are produced in the form of duromers or soluble thermoplastics which can be subjected to various shaping processes directly in solution or as a melt, e.g. casting, spinning to fibres, drawing of films, production of coatings by various coating processes such as dip-coating or spin-coating, before these are converted to, for example, silicon carbonitride ceramics.

The invention additionally relates to silicon borocarbonitride ceramics made from the oligo- or polyborocarbosilazanes of the invention comprising N—Si—C—B—N bonds.

The invention additionally relates to a process for preparing silicon borocarbonitride ceramics of the invention, in which at least one of the oligo- or polyborocarbosilazanes of the invention is pyrolysed in an ammonia or inert gas atmosphere at temperatures between $-200$ and $2000°$ C., preferably 400 and $2000°$ C., and is then calcined in an ammonia or inert gas atmosphere at temperatures between 800 and $2000°$ C.

In a preferred embodiment of the process according to the invention, the oligo- or polyborocarbosilazanes are heated to temperatures between 100 and $600°$ C. and kept at this temperature for several hours. They are then preferably calcined to remove hydrogen at temperatures between 1200 and $1500°$ C. in a nitrogen or argon atmosphere.

The invention additionally relates to the use of the oligo- or polyborocarbosilazanes of the invention for preparing ceramic powders, ceramic coatings and ceramic shaped bodies, films, fibres or coatings.

The invention is described by way of example below, without any restriction to be implied therein.

The invention is further described in the following illustrative examples in which all parts and percentages are by weight unless otherwise indicated.

ILLUSTRATIVE EXAMPLES

Example 1

Synthesis of 1,1-(trichlorosilyl)(dichloroboryl)ethane
Reaction equation:

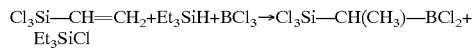

Experimental procedure:
triethylsilane 93.2 mmol≙10.84 g
boron trichloride 93.2 mmol≙10.95 g
trichlorovinylsilane 93.2 mmol≙15.1 g 10.95 g of boron trichloride were condensed into a 100 ml three-neck flask which was provided with a dropping funnel and pressure equilibration. The receiver was cooled in the course of this to $-65°$ C. In the course of 15 min, a mixture of 10.84 g of triethylsilane and 15.1 g of trichlorovinylsilane was added dropwise. The reaction mixture was then allowed to warm up to room temperature and volatile byproducts were drawn off into a cold trap at 20 mbar. The mixture was then subjected to fractional distillation. The product was obtained in one fraction together with triethylchlorosilane.
$^{11}$B-NMR spectrum: $\delta=66.9$ ppm ($BCl_2$)
$^{13}$C-NMR spectrum: $\delta=11.21$ ppm ($CH_3$), $\delta=34.1$ ppm (CH)
$^{1}$H-NMR spectrum: $\delta=1.43$ ppm ($CH_3$), $\delta=2.19$ ppm (CH)
$^{29}$Si-NMR spectrum: $\delta=13.23$ ppm

Example 2

Synthesis of 1,1-(dichloromethylsilyl)(dichloroboryl)ethane
Reaction equation:

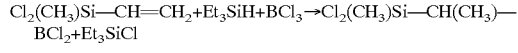

Experimental procedure:
triethylsilane 93.2 mmol≙10.84 g
boron trichloride 93.2 mmol≙10.95 g
dichloromethylvinylsilane 93.2 mmol≙13.2 g 10.95 g of boron trichloride were condensed into a 100 ml three-neck flask which was provided with a dropping funnel and pressure equilibration. The receiver was cooled in the course of this to $-65°$ C. In the course of 15 min, a mixture of 10.84 g of triethylsilane and 13.2 g of dichloromethylvinylsilane was added dropwise. The reaction mixture was then allowed to warm up to room temperature and volatile byproducts were drawn off into a cold trap at 20 mbar. The mixture was then subjected to fractional distillation. The product was obtained in one fraction together with triethylchlorosilane.
$^{1}$H-NMR spectrum: $\delta=1.40$ ppm (d) ($CH_3$), $\delta=0.88$ ppm (s) ($SiCH_3$), $\delta=1.99$ ppm (q) (CH)
$^{13}$C-NMR spectrum: $\delta=5.63$ ppm ($SiCH_3$), $\delta=11.56$ ppm ($CH_3$), $\delta=31.01$ ppm (CH)
$^{29}$Si-NMR spectrum: $\delta=26.78$ ppm
$^{11}$B-NMR spectrum: $\delta=67.66$ ppm

Example 3

Synthesis of 1,1-(chlorodimethylsilyl)(dichloroboryl)ethane
Reaction equation:

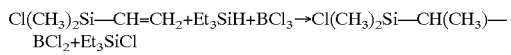

Experimental procedure:

triethylsilane 93.2 mmol≙10.84 g
boron trichloride 93.2 mmol≙10.95 g
chlorodimethylvinylsilane 93.2 mmol≙11.2 g 10.95 g of boron trichloride were condensed into a 100 ml three-neck flask which was provided with a dropping funnel and pressure equilibration. The receiver was cooled in the course of this to −65° C. In the course of 15 min, a mixture of 10.84 g of triethylsilane and 11.2 g of chlorodimethylvinylsilane was added dropwise. The reaction mixture was then allowed to warm up to room temperature and volatile byproducts were drawn off into a cold trap at 20 mbar. The mixture was then subjected to fractional distillation. The product was obtained in one fraction together with triethylchlorosilane.

$^1$H-NMR spectrum: δ=1.31 ppm (d) (CH$_3$), δ=1.78 ppm (q) (CH), δ=0.52 ppm (s) (Si(CH$_3$)$_2$)

$^{13}$C-NMR spectrum: δ=1.87 ppm (Si(CH$_3$)$_2$), δ=11.61 ppm (CH$_3$), δ=30.02 ppm (CH) δ=2.05 ppm (Si(CH$_3$)$_2$)

$^{29}$Si-NMR spectrum: δ=28.40 ppm $^{11}$B-NMR spectrum: δ=67.90 ppm

Example 4

Synthesis of 1,1-(trichlorosilyl)(dichloroboryl)ethane

Reaction equation:

Experimental procedure:

chlorodimethylsilane 0.2 mol=19.7 g
boron trichloride 0.24 mol=20 ml
trichlorovinylsilane 0.2 mol=33.3 g 20 ml of boron trichloride were condensed into a 250 ml three-neck flask which was provided with a dropping funnel and pressure equilibration. The receiver was cooled in the course of this to −65° C. In the course of 40 min, a mixture of 19.7 g of chlorodimethylsilane (98% pure) and 33.3 g of trichlorovinylsilane (97% pure) was added dropwise. The reaction mixture was then allowed to warm up to room temperature and volatile byproducts were drawn off into a cold trap at 20 mbar. The mixture was then subjected to fractional distillation. The product was obtained at high purity at 47 to 49° C. and 10 mbar. The yield was 62.1%.

$^{11}$B-NMR spectrum: δ=66.9 ppm (BCl$_2$)
$^{13}$C-NMR spectrum: δ=11.21 ppm (CH$_3$), δ=34.1 ppm (CH)
$^1$H-NMR spectrum: δ=1.43 ppm (CH$_3$), δ=2.19 ppm (CH)
$^{29}$Si-NMR spectrum: δ=13.23 ppm Although the present invention has been described in detail with reference to certain preferred versions thereof, other variations are possible. Therefore, the spirit and scope of the appended claims should not be limited to the description of the versions contained therein.

What is claimed is:

1. A molecular silylalkylborane of the general structural formula

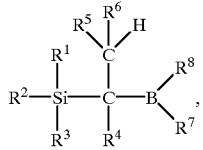

wherein the Si atom is coordinated to 3 radicals, R$^1$, R$^2$, and R$^3$ and the B atom is coordinated to 2 radicals, R$^7$, R$^8$, and silicon and boron are linked by a C(CR$^5$R$^6$H)(R$^4$) bridge, where R$^1$ to R$^3$ independently of one another comprise a component selected from the group consisting of C$_1$–C$_6$-alkyl groups, vinyl groups, phenyl groups, hydrogen and halogen, R$^4$ to R$^6$ comprise a component selected from the group consisting of C$_1$–C$_6$-alkyl groups, vinyl groups phenyl groups and hydrogen and R$^7$ and R$^8$ comprise a component selected from the group consisting of chloride and bromide.

2. The molecular silylalkylborane according to claim 1, wherein

R$^1$ to R$^3$ comprise Cl or CH$_3$,
R$^4$ comprises H, R$^5$ comprises CH$_3$ and
R$^6$ and R$^7$ comprise Cl.

3. Process for preparing the molecular silylalkylborane according to claim 1 wherein a halogenovinylsilane of the formula

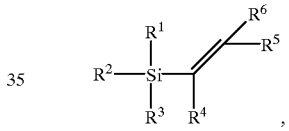

wherein R$^1$ to R$^3$ comprise a component selected from the group consisting of H, halogen, C$_1$–C$_6$-alkyl groups, vinyl groups and phenyl groups and R$^4$ to R$^6$ comprise a component selected from the group consisting of H, C$_1$–C$_6$-alkyl groups, vinyl groups and phenyl groups, is reacted with dihalogenoboranes, wherein the halogen comprises a component selected from the group consisting of Cl and bromine, at a temperature ranging from about −80 to 200° C., and the reaction mixture is then subjected to fractional distillation at a pressure ranging from about 1 mbar to 20 mbar.

4. The process for preparing the molecular silylalkylborane according to claim 3, wherein the dihalogenoboranes are produced in situ from silanes of the formula R$_x^1$R$_y^2$SiH$_{4-x-y}$, wherein x+y<4, R$^1$ comprises a component selected from the group consisting of C$_1$–C$_6$-alkyl groups, and phenyl groups and R$^2$ comprises a component selected from the group consisting of halogen and boron trihalides.

5. An oligo- or polyborocarbosilazane made from the molecular silylalkylborane according to claim 1, wherein each silicon atom has at least one carbon atom in the first coordination sphere and this carbon atom is bound to a boron atom, each boron atom in addition being further bound to 2 nitrogen atoms.

6. A silicon borocarbonitride ceramic made from the oligo- or polyborocarbosilazane of claim 5, wherein the ceramic comprises N—Si—C—B—N bonds.

7. Process for preparing a silicon borocarbonitride ceramic, wherein at least one oligo- or polyborocarbosilazane according to claim 5 is pyrolysed in an ammonia or inert gas atmosphere at a temperature ranging from −200 and 2000° C. and is then calcined in an ammonia or inert gas atmosphere at a temperature ranging from 800 and 2000° C.

8. A process for preparing a polymeric oligo- or polycarborocarbosilazane, wherein each silicon atom of the a polymeric oligo- or polycarborocarbosilazane has at least one carbon atom in the first coordination sphere and this carbon atom is bound to a boron atom, each boron in addition being further bound to 2 nitrogen atoms, the process comprising the step of reacting A) a molecular silylalkylborane according to claim 1 with
B) at least 10 moles of a component comprising at least one member selected from the group consisting of ammonia and an organylamine of the formula $H_2NR$, wherein R comprises a component selected from the group consisting of H, C, $C_1$–$C_8$-alkyl groups, vinyl groups and phenyl groups, per mole of the molecular sililalkylborane in a solvent at a temperature ranging from −80 to 300° C.

* * * * *